(12) United States Patent
Willis

(10) Patent No.: US 12,023,488 B2
(45) Date of Patent: Jul. 2, 2024

(54) IMPLANTABLE STIMULATION ASSEMBLIES HAVING TISSUE ENGAGEMENT MECHANISMS, AND ASSOCIATED SYSTEMS AND METHODS

(71) Applicant: EBR Systems, Inc., Sunnyvale, CA (US)

(72) Inventor: Nathaniel Parker Willis, Sunnyvale, CA (US)

(73) Assignee: EBR SYSTEMS, INC., Sunnyvale, CA (US)

( * ) Notice: Subject to any disclaimer, the term of this patent is extended or adjusted under 35 U.S.C. 154(b) by 315 days.

(21) Appl. No.: 17/404,252

(22) Filed: Aug. 17, 2021

(65) Prior Publication Data

US 2022/0047865 A1    Feb. 17, 2022

Related U.S. Application Data

(60) Provisional application No. 63/066,694, filed on Aug. 17, 2020.

(51) Int. Cl.
*A61N 1/05* (2006.01)
*A61N 1/37* (2006.01)
(Continued)

(52) U.S. Cl.
CPC ......... *A61N 1/0573* (2013.01); *A61N 1/3706* (2013.01); *A61N 1/371* (2013.01);
(Continued)

(58) Field of Classification Search
CPC .............................. A61N 1/059; A61N 1/0592
See application file for complete search history.

(56) References Cited

U.S. PATENT DOCUMENTS 3,659,615 A    5/1972    Enger
3,693,627 A    9/1972    Berkovits
(Continued)

FOREIGN PATENT DOCUMENTS

DE    4330680 A1    3/1995
JP    H06505662 A    6/1994
(Continued)

OTHER PUBLICATIONS

International Search Report and Written Opinion dated Jan. 11, 2022 in International Application No. PCT/US21/46376, 14 pages.
(Continued)

*Primary Examiner* — Michael W Kahelin
(74) *Attorney, Agent, or Firm* — Perkins Coie LLP

(57) ABSTRACT

The present technology is generally directed to medical implants, such as stimulation assemblies for stimulating heart tissue. In some embodiments, a stimulation assembly includes a body, circuitry positioned at least partially within the body, an electrode coupled to the body, and a hook mechanism coupled to the body. The stimulation assembly can be implanted at cardiac tissue of a patient such that the electrode electrically contacts the tissue. The circuitry can be configured to receive acoustic energy and convert the acoustic energy to electrical energy, and the electrode can deliver the electrical energy to the tissue to stimulate the tissue. The hook mechanism can be configured to engage the tissue to pull the tissue and the electrode toward and into engagement with one another.

20 Claims, 12 Drawing Sheets

(51) Int. Cl.
*A61N 1/372* (2006.01)
*A61N 1/378* (2006.01)
*H02J 50/15* (2016.01)

(52) U.S. Cl.
CPC ....... *A61N 1/37205* (2013.01); *A61N 1/3787* (2013.01); *A61N 2001/058* (2013.01); *A61N 2001/0582* (2013.01); *H02J 50/15* (2016.02)

(56) References Cited

U.S. PATENT DOCUMENTS

| | | | |
|---|---|---|---|
| 3,698,398 A | 10/1972 | Berkovits | |
| 3,735,756 A | 5/1973 | Richards et al. | |
| 3,832,994 A | 9/1974 | Bicher et al. | |
| 3,857,382 A | 12/1974 | Williams et al. | |
| 3,939,844 A | 2/1976 | Peuignot et al. | |
| 3,942,534 A | 3/1976 | Allen et al. | |
| 4,181,133 A | 1/1980 | Kolenik et al. | |
| 4,256,115 A | 3/1981 | Bilitch | |
| 4,265,228 A | 5/1981 | Zoll | |
| 4,280,502 A | 7/1981 | Baker, Jr. et al. | |
| 4,306,560 A * | 12/1981 | Harris .................. A61N 1/0587 607/129 | |
| 4,561,442 A | 12/1985 | Vollmann et al. | |
| 4,577,633 A | 3/1986 | Forester et al. | |
| 4,690,144 A | 9/1987 | Rise et al. | |
| 4,830,006 A | 5/1989 | Haluska et al. | |
| 5,018,523 A | 5/1991 | Bach, Jr. et al. | |
| 5,063,928 A | 11/1991 | Grevis et al. | |
| 5,103,129 A | 4/1992 | Slayton et al. | |
| 5,113,859 A | 5/1992 | Funke | |
| 5,141,588 A | 8/1992 | VanBuskirk | |
| 5,165,403 A | 11/1992 | Mehra | |
| 5,170,784 A | 12/1992 | Ramon et al. | |
| 5,174,289 A | 12/1992 | Cohen | |
| 5,186,177 A | 2/1993 | O'Donnell et al. | |
| 5,193,539 A | 3/1993 | Schulman et al. | |
| 5,292,338 A | 3/1994 | Bardy et al. | |
| 5,377,166 A | 12/1994 | Kuhn | |
| 5,405,367 A | 4/1995 | Schulman et al. | |
| 5,411,535 A | 5/1995 | Fujii et al. | |
| 5,433,731 A | 7/1995 | Hoegnelid et al. | |
| 5,590,657 A | 1/1997 | Cain et al. | |
| 5,674,251 A | 10/1997 | Combs et al. | |
| 5,749,909 A | 5/1998 | Schroeppel et al. | |
| 5,751,539 A | 5/1998 | Stevenson et al. | |
| 5,757,104 A | 5/1998 | Getman et al. | |
| 5,766,227 A | 6/1998 | Nappholz et al. | |
| 5,800,464 A | 9/1998 | Kieval | |
| 5,814,089 A | 9/1998 | Stokes et al. | |
| 5,817,130 A | 10/1998 | Cox et al. | |
| 5,844,349 A | 12/1998 | Oakley et al. | |
| 5,871,506 A | 2/1999 | Mower | |
| 5,879,303 A | 3/1999 | Averkiou et al. | |
| 5,935,158 A | 8/1999 | Holmstrom et al. | |
| 5,978,204 A | 11/1999 | Stevenson et al. | |
| 5,998,910 A | 12/1999 | Park et al. | |
| 6,037,704 A | 3/2000 | Welle | |
| 6,070,101 A | 5/2000 | Struble et al. | |
| 6,078,837 A | 6/2000 | Peterson et al. | |
| 6,110,098 A | 8/2000 | Renirie et al. | |
| 6,141,588 A | 8/2000 | Renirie et al. | |
| 6,223,079 B1 | 4/2001 | Bakels et al. | |
| 6,233,484 B1 | 5/2001 | Ben-Haim et al. | |
| 6,264,611 B1 | 7/2001 | Ishikawa et al. | |
| 6,330,475 B1 | 12/2001 | Renirie et al. | |
| 6,366,816 B1 | 4/2002 | Marchesi | |
| 6,408,205 B1 | 6/2002 | Renirie et al. | |
| 6,424,234 B1 | 7/2002 | Stevenson et al. | |
| 6,425,869 B1 | 7/2002 | Rafter et al. | |
| 6,439,236 B1 | 8/2002 | Porter et al. | |
| 6,445,953 B1 | 9/2002 | Bulkes et al. | |
| 6,464,680 B1 | 10/2002 | Brisken et al. | |
| 6,496,715 B1 | 12/2002 | Lee et al. | |
| 6,527,729 B1 | 3/2003 | Turcott | |
| 6,534,895 B2 | 3/2003 | Kadota et al. | |
| RE38,119 E | 5/2003 | Mower | |
| 6,628,989 B1 | 9/2003 | Penner et al. | |
| 6,645,145 B1 | 11/2003 | Dreschel et al. | |
| 6,647,292 B1 | 11/2003 | Bardy et al. | |
| 6,654,638 B1 | 11/2003 | Sweeney | |
| 6,671,547 B2 | 12/2003 | Lyster et al. | |
| 6,834,204 B2 | 1/2004 | Osteroff et al. | |
| 6,707,230 B2 | 3/2004 | Smith et al. | |
| 6,721,597 B1 | 4/2004 | Bardy et al. | |
| 6,728,576 B2 | 4/2004 | Thompson et al. | |
| 6,754,528 B2 | 6/2004 | Bardy et al. | |
| 6,754,531 B1 | 6/2004 | Kroll et al. | |
| 6,764,446 B2 | 7/2004 | Wolinsky et al. | |
| 6,788,974 B2 | 9/2004 | Bardy et al. | |
| 6,795,732 B2 | 9/2004 | Stadler et al. | |
| 6,856,835 B2 | 2/2005 | Bardy et al. | |
| 6,970,742 B2 | 11/2005 | Mann et al. | |
| 7,006,864 B2 | 2/2006 | Echt et al. | |
| 7,010,350 B2 | 3/2006 | Kralik | |
| 7,043,292 B2 | 5/2006 | Tarjan et al. | |
| 7,050,849 B2 | 5/2006 | Echt et al. | |
| 7,160,258 B2 | 1/2007 | Imran et al. | |
| 7,184,830 B2 | 2/2007 | Echt et al. | |
| 7,200,437 B1 | 4/2007 | Nabutovsky | |
| 7,283,874 B2 | 10/2007 | Penner et al. | |
| 7,349,740 B2 | 3/2008 | Soykan et al. | |
| 7,489,967 B2 | 2/2009 | Von Arx et al. | |
| 7,499,759 B2 * | 3/2009 | Coe .................. A61N 1/0587 607/129 | |
| 7,558,631 B2 | 7/2009 | Cowan et al. | |
| 7,606,621 B2 | 10/2009 | Brisken et al. | |
| 7,610,092 B2 | 10/2009 | Cowan et al. | |
| 7,751,881 B2 | 7/2010 | Cowan et al. | |
| 7,848,815 B2 | 12/2010 | Brisken et al. | |
| 7,890,173 B2 | 2/2011 | Brisken et al. | |
| 7,894,907 B2 | 2/2011 | Cowan et al. | |
| 7,996,087 B2 | 8/2011 | Cowan et al. | |
| 8,315,701 B2 | 11/2012 | Cowan et al. | |
| 8,718,773 B2 | 5/2014 | Willis et al. | |
| 9,008,776 B2 | 4/2015 | Cowan et al. | |
| 9,283,392 B2 | 3/2016 | Moore et al. | |
| 9,343,654 B2 | 5/2016 | Moore et al. | |
| 9,616,237 B2 | 4/2017 | Pare et al. | |
| 9,731,138 B1 | 8/2017 | Stadler et al. | |
| 11,266,845 B2 | 3/2022 | Kim et al. | |
| 2002/0077673 A1 | 6/2002 | Penner et al. | |
| 2003/0013974 A1 | 1/2003 | Natarjan et al. | |
| 2003/0069625 A1 | 4/2003 | Ley et al. | |
| 2004/0015104 A1 | 1/2004 | Goldberger | |
| 2004/0162501 A1 | 8/2004 | Imran et al. | |
| 2004/0167580 A1 | 8/2004 | Mann et al. | |
| 2004/0172083 A1 | 9/2004 | Penner et al. | |
| 2004/0204744 A1 | 10/2004 | Penner et al. | |
| 2004/0260346 A1 | 12/2004 | Overall et al. | |
| 2005/0070962 A1 | 3/2005 | Echt et al. | |
| 2006/0009831 A1 | 1/2006 | Lau et al. | |
| 2006/0106442 A1 | 5/2006 | Richardson et al. | |
| 2006/0135999 A1 | 6/2006 | Bodner et al. | |
| 2006/0155338 A1 * | 7/2006 | Mongeon ............... A61N 1/371 607/9 | |
| 2006/0161061 A1 | 7/2006 | Echt et al. | |
| 2006/0224067 A1 | 10/2006 | Giftakis et al. | |
| 2006/0241701 A1 | 10/2006 | Markowitz et al. | |
| 2007/0032749 A1 | 2/2007 | Overall et al. | |
| 2007/0088394 A1 | 4/2007 | Jacobson | |
| 2007/0088397 A1 | 4/2007 | Jacobson | |
| 2007/0088398 A1 | 4/2007 | Jacobson | |
| 2007/0150009 A1 | 6/2007 | Kveen et al. | |
| 2007/0232936 A1 | 10/2007 | Mann et al. | |
| 2007/0260286 A1 | 11/2007 | Giftakis et al. | |
| 2007/0265677 A1 | 11/2007 | Giftakis et al. | |
| 2009/0082828 A1 | 3/2009 | Ostroff | |
| 2018/0140850 A1 | 5/2018 | Linder et al. | |

(56) References Cited

U.S. PATENT DOCUMENTS

| | | | |
|---|---|---|---|
| 2018/0154164 A1 | 6/2018 | Bodner et al. | |
| 2020/0338356 A1 | 10/2020 | Anderson et al. | |

FOREIGN PATENT DOCUMENTS

| | | | |
|---|---|---|---|
| JP | 2002538934 A | 11/2002 | |
| JP | 2003218805 A | 7/2003 | |
| JP | 2004512106 A | 4/2004 | |
| WO | 9961058 A1 | 12/1999 | |
| WO | 03070323 A1 | 8/2003 | |
| WO | 2004089465 A1 | 10/2004 | |
| WO | 2004101062 A2 | 11/2004 | |
| WO | 2004101062 A3 | 3/2005 | |
| WO | 2009006531 A1 | 1/2009 | |

OTHER PUBLICATIONS

Abraham et al., for the MIRACLE study group, "Cardiac Resynchronization in Chronic Heart Failure," N Engl J Med, 2002;346: 1845-53.
ACC/AHA Task Force on Practice Guidelines, "Evaluation and Management of Chronic Heart Failure in the Adult," JACC 2002; 38: 2101-13.
Allessie et al., "Regional Control of Atrial Fibrillation by Rapid Pacing in Conscious Dogs," Circulation 1991 ;84: 1689-97.
Ansalone et al., "Bi-ventricular pacing I heart failure:back to basics in the pathophysiology of left bundle branch block to reduce the number of nonresponders," Am J Cardiol 2003;91 :55F-61F.
Auricchio eta I., "Cardiac resynchronization therapy: current state of the art," Circulation 2004; I 09:300-307.
Bardy et al., "The Totally Subcutaneous ICD System (The S-ICD)," PCAE. 2002, 24, 578.
Becker et al., "Suppression of Atrial Fibrillation by Multisite and Septal Pacing in a Novel Experimental Model", Cardiovascular Research 2001;54:476-481.
Bradley et al., "Suppression of Atrial Fibrillation by Multisite and Septal Pacing in a Novel Experimental Model," Cardiovascular Research 2001; 54(2): 476-481.
Camm et al., Chaper 6: Nonpharmaceutical treatment of atrial fibrillation, In Atrial Fibrillation. Facts from Yesterday—Ideas for tomororw. Future Publishing Company, Inc., Armonk, NY, 1994, pp. 125-147.
Dalecki et al., "Effects of Pulsed Ultrasound on the Frog Heart: I. Thresholds for Changes in Cardiac Rhythm and Aortic Pressure," Ultrasound in Med. & Biol. 1993; 19: 385-390.
Dalecki et al., "Effects of Pulsed Ultrasound on the Frog Heart: II. An Investigation of Heating as a Potential Mechanism," Ultrasound in Med. & Biol. 1993; 19: 391-398.
Dalecki et al., "Thresholds for premature ventricular contractions in frog hearts exposed to lithotripter fields," Ultrasound in Med. & Biol. 1991; 17:341-346.
Daoud et al., "Implantation Techniques and Chronic Lead Parameters of Bivnetricular Pacing Dual-chambers Defibrillators," J Cardiovasc Electrophysiology 2002; 13: 964-970.
Daubert et al., "Permanent Left Ventricular Pacing with Transvenous Leads Inserted Into the Coronary Veins," PACE 1998; 21: 239-245.
Daubert et al., "Use of Specifically Designed Coronary Sinus Leads for Permanent Left Ventricular Pacing: Preliminary Experience," PACE 1997; 20: II-NASPE Abstract 17, Apr. 1997.
DAVID Trial Investigators, "The Dual Chamber and VVI Implantable Defibrillator (DAVID) Trial," JAMA 2002;288:3115-3123.
Deshmukh et al., "Direct His-bundle pacing: present and future," PACE 2004;27 [Pt.II]:862-70.
Ellenbogen et al., "Detection and Management of an Implantable Cardioverter Defibrillator Lead Failure," JACC 2003; 41: 73-80.
European Search Report and Search Opinion dated Mar. 23, 2012 in European Patent Application No. 07841364.8.
European Search Report and Search Opinion dated May 4, 2010 in European Patent Application No. 05855143, 8 pages.
Extended European Search Report dated Mar. 26, 2008 in European Patent Application No. 05855395.9, 6 pages.
Feldman et al., "Comparison of medical therapy, resynchronization and defibrillation therapies in heart failure trial (COMPANION)," Presented at ACC 2003 Laet Breaking Clinical Trials, 1 page.
Franz, "Mechano-electrical feedback in ventricular myocardium," Cardiovascular Research. 1996; 32: 15-24.
Gregoratos et al., ACC/AHA/NASPE 2002 guideline update for implanation of cardiac pacemakers and antiarrhythmia devices: a report of the American College of Cardiology/American Heart Association Task Force on Practice Guidelines (ACC/AHA/NASPE Committee to Update the 1998 Pacemaker Guidelines). Circulation 2002; 106: 2145-2161.
Hu et al., "Stretch-Activated lon Channels in the Heart," J. Mol. Cell Cardiol. 1997; 29: 1511-1523.
International Search Report and Written Opinion dated Apr. 7, 2008 in International Application No. PCT/US07/76812, 8 pages.
International Search Report and Written Opinion dated Jun. 23, 2008 in International Application No. PCT/US05/46532, 8 pages.
Johnson et al., Adaptive Pacing during Ventricular Fibrillation, PACE 2003;26:1824-36.
Kalman et al., "Regional Entrainment of Atrial Fibrillation in Man", J Cardiovasc Electrophysiol 1991;7:867-76.
Kass et al., "Improved Left Ventricular Mechanics from Acute VDD Pacing in Patients with Dilated Cardiomyopathy and Ventricular Conduction Delay," Circulation 1999;99: 1567-73.
Kenknight B.H. et al., "Regional Capture of Fibrillating Ventricular Myocardium" Circ Res 1999;77:849-55.
Kohl et al., "Stretch-Induced Changes in Heart Rate and Rhythm: Clinical Observations, Experiments and Mathematical Models." Progress in Biophysics & Molecular Biology, 1999; 91: 91-138.
Kohl et al., "Sudden Cardiac Death by Commotio Cordis: Role of Merchano-Electrical Feedback," Cardiovascular Research, 2001; 50: 280-289.
Leclercq et al., "Acute Hemodynamic Effects of Biventricular DDD Pacing in Patients with End-Stage Heart Failure," JACC 1998; 32: 1825-1831.
Leclercq et al., "Systolic Improvement and Mechanical Resynchronization does not Require Electrical Synchrony in the Dilated Failing Heart with Left-Bundle-Branch Block," Circulation 2002; 106: 1760-1763.
Leclercq et al., "Is Dual Site Better than Single Site Atrial Pacing in the Prevention of Atrial Fibrillation?" PACE 2000;23 2102-7.
Lee et al., "Effect of implantable Defibrillators of Arrhythmic Events and Mortality in the Multicenter Unsustained Tachycardia Trial," Circulation. 2002; 106: 233-238.
Linde et al., "Long-Term Benefits of Biventricular Pacing in Congestive Heart Failure: From the Multisite Stimulation in Cardiomyopathy (MUSTIC) Study," J Am Coll Cardiol 2002; 40: 111-118.
Miracle Trial Investigators, "Combined Cardiac Resynchronization and Implantable Cardioversion Defibrillation in Advanced Heart Failure:the Miracle ICD Trial," JAMA 2003; 289: 2685-2694.
Mirza et al., "Biatrial Pacing for Paroxysmal Atrial Fibrillation", J Am Coll Cardiol 2002;40:457-463.
Moss et al., "Prophylactic Implantation of a Defibrillator in Patients with Myocardial Infarction and Reduced Ejection Fraction," N Engl J Med. 2002; 346: 877-933.
Niehaus et al., "Non-Contact Cardiac Stimulation with locused Ultrasound Pulses," PACE 2003: 216: 1023.
Nielsen et al., "A Randomized Comparison of Atrial and Dual-Chambered Pacing in 177 Consecutive Patients with Sick Sinus Syndrome," J Am Coll Cardiol 2003; 42: 614-623.
Nolte et al., "Mechanically Induced Ventricular Extrasystoles in the Isolated Perfused Guinea-Pig Heart," Arzneim.-Forsch/drug Research. 1987; 37(11): 1025-1029.
Office Action dated Jan. 3, 2012 for U.S. Appl. No. 12/554,257.
Office Action dated May 14, 2012 for U.S. Appl. No. 12/554,257.
Office Action dated Jun. 23, 2008 for U.S. Appl. No. 11/535,857.
Office Action dated Sep. 14, 2010 for U.S. Appl. No. 12/554,234.
Office Action dated Nov. 12, 2008 for U.S. Appl. No. 11/535,857.
Peschar et al., "Left ventricular septal and apex pacing for optimal pump function in canine hearts," J Am Coll Cardiol 2003;41:1218-26.

(56) References Cited

OTHER PUBLICATIONS

Reiter et al., "Effects of Mechano-Electrical Feedback: Potential Arrhythmogenic Influence in Patients with Congestive Heart Failure," Cardiovascular Research, 1996; 32: 44-51.
Smailys et al., "Investigation of the Possibilities of cardiac Defibrillation by Ultrasound," Resuscitation, 1981; 9: 233-242.
Sowton., "Clinical Results with the Tachylog Antitachycardia Pacemaker", PACE 1984;7(Part 11):1313-1317.
Tacker, Chapter 1: Fibrillation causes and criteria for defibrillation. In Defibrillation of the Heart. Tacker, WA, ed. Mosby-Year Book, Inc., St. Louis, Missouri, 1994, pp. 1-14.
The Antiarrhythmics Versus Implantable Defibrillators (AVID) Investigators, "A Comparison of Antiarrhythmic Drug Therapy with Implantable Defibrillators in Patients Resuscitated from Near Fatal Ventricular Arrhythmias," N Engl J Med, 1997; 337: 1576-1583.
Valls-Bertaults et al., "Adverse Events with Transvenous Left Ventricular Pacing in Patients with Severe Heart Failure: Early Experience from a Single Centre," Europace, 2001; 3: 60-63.
Warren et al., "Clinical Evaluation of Automatic Tachycardia Diagnosis by an Implanted Device", PACE 1986;9 (Part 11):1079-1083.

\* cited by examiner

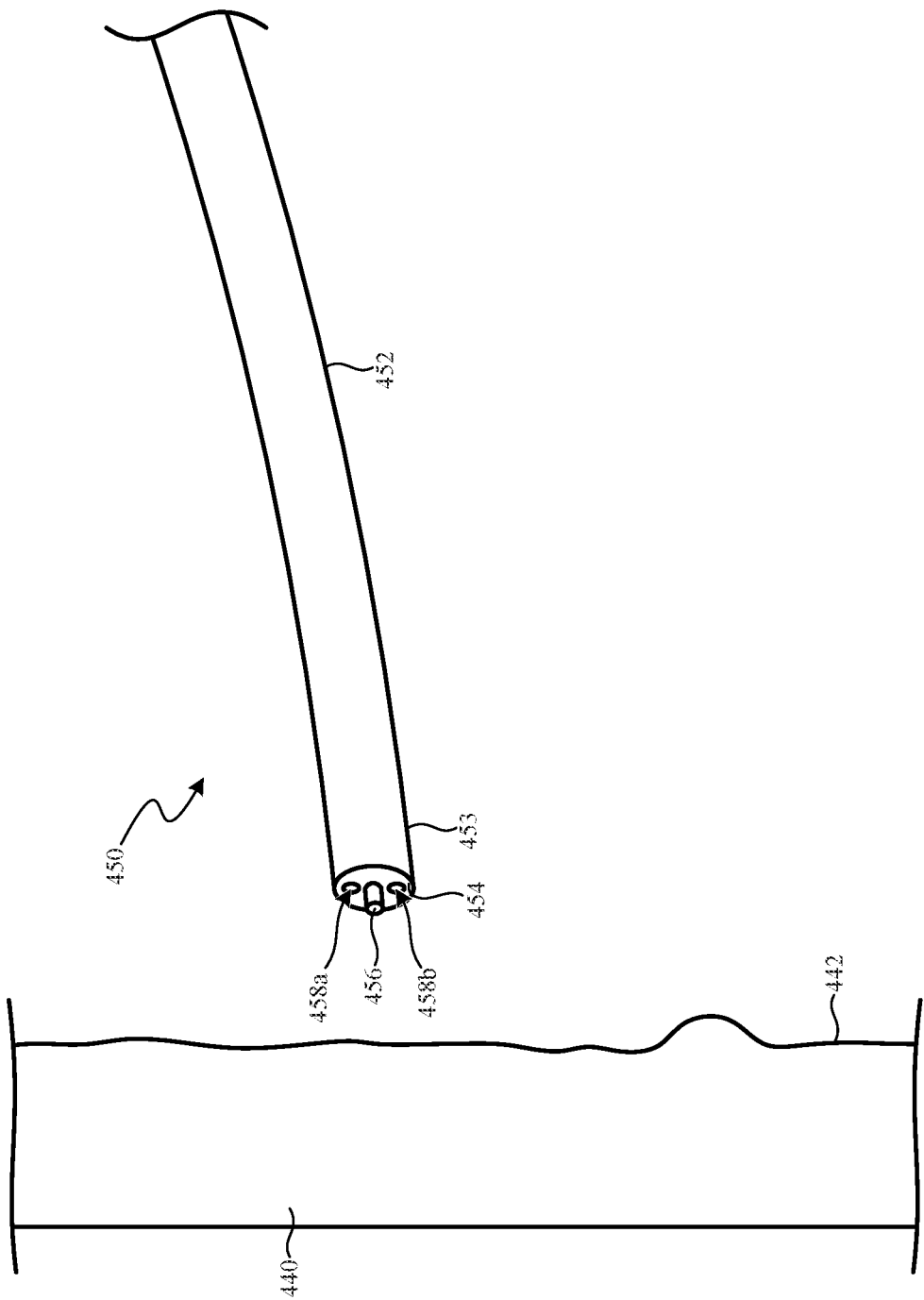

IMPLANTABLE STIMULATION ASSEMBLIES HAVING TISSUE ENGAGEMENT MECHANISMS, AND ASSOCIATED SYSTEMS AND METHODS

CROSS-REFERENCE TO RELATED APPLICATION

This application claims the benefit of U.S. Provisional Patent Application No. 63/066,694, filed Aug. 17, 2020, and titled "ENDOCARDIAL PACING ELECTRODES WITH TISSUE ENGAGEMENT MECHANISMS," which is incorporated herein by reference in its entirety.

TECHNICAL FIELD

The present technology generally relates to methods, systems, and devices for stimulating cardiac tissue, and more particularly to implantable stimulation assemblies with tissue engagement mechanisms for engaging tissue.

BACKGROUND

Electrical stimulation of body tissue is used throughout medicine for treatment of both chronic and acute conditions. Among many examples, peripheral muscle stimulation is reported to accelerate healing of strains and tears, bone stimulation is likewise indicated to increase the rate of bone regrowth/repair in fractures, and nerve stimulation is used to alleviate chronic pain. Further there is encouraging research in the use of electrical stimulation to treat a variety of nerve and brain conditions, such as essential tremor, Parkinson's disease, migraine headaches, functional deficits due to stroke, and epileptic seizures.

Cardiac pacemakers and implantable defibrillators are examples of commonly implanted device utilizing electrical stimulation to stimulate cardiac and other tissues. A pacemaker is a battery-powered electronic device implanted under the skin, connected to the heart by an insulated metal lead wire with a tip electrode. Pacemakers were initially developed for and are most commonly used to treat slow heart rates (bradycardia), which may result from a number of conditions. More recently, advancements in pacemaker complexity, and associated sensing and pacing algorithms have allowed progress in using pacemakers for the treatment of other conditions, notably heart failure (HF) and fast heart rhythms (tachyarrhythmia/tachycardia).

Electrical energy sources connected to electrode/lead wire systems have typically been used to stimulate tissue within the body. The use of lead wires is associated with significant problems such as complications due to infection, lead failure, and electrode/lead dislodgement. The requirement for leads to accomplish stimulation also limits the number of accessible locations in the body. The requirement for leads has also limited the ability to stimulate at multiple sites (multisite stimulation).

Wireless stimulation electrodes are often secured to target tissue by pushing an anchor mechanism of the electrode into the tissue to secure the electrode thereto. However, when the target tissue has a complex structure—such as when the tissue is endocardial wall tissue consisting of complex trabeculae, papillary muscles, chordae, etc.—pushing the electrode into the tissue may improperly secure the electrode to the tissue.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

FIGS. 4A-4I are side views of a distal portion of a delivery system during different stages of a procedure to implant a receiver-stimulator within a patient in accordance with embodiments of the present technology.

DETAILED DESCRIPTION

Figure 1:
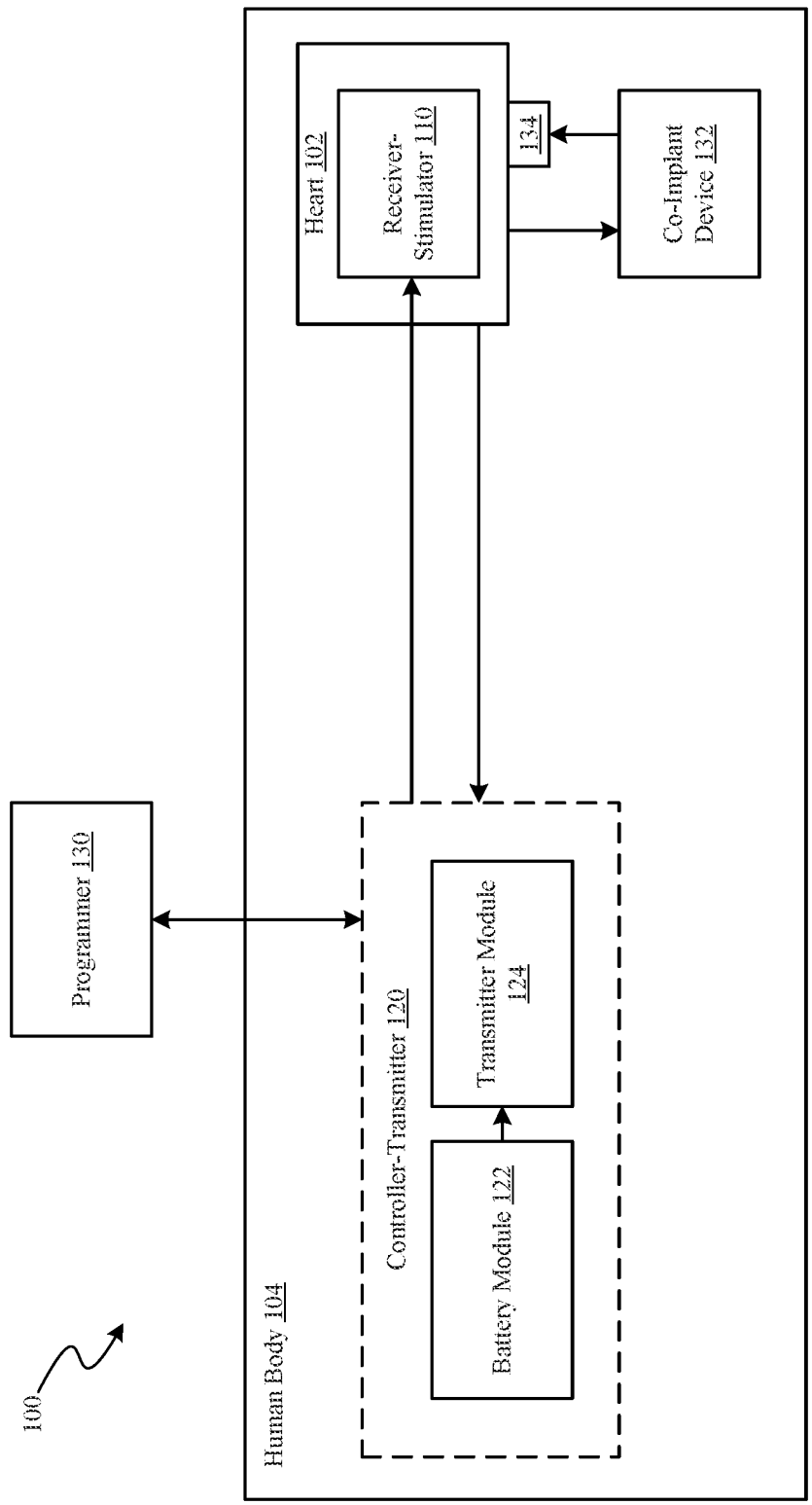
FIG. 1 is a schematic diagram of a tissue stimulation system in accordance with embodiments of the present technology.

Aspects of the present disclosure are directed generally to implantable stimulation assemblies (which can be referred to as receiver-stimulators, stimulation electrodes, pacing electrodes, and the like) including mechanisms for engaging tissue of a patient, such as endocardial tissue, and associated systems and methods. In several of the embodiments described below, for example, a stimulation assembly includes a body, circuitry positioned at least partially within the body, an electrode coupled to the body, and a hook mechanism coupled to the body. The circuitry can be configured to receive acoustic energy and convert the acoustic energy to electrical energy, and the electrode can deliver the electrical energy to the tissue of the patient. The hook mechanism can be configured to engage the tissue to pull the tissue and the electrode toward and into engagement with one another. For example, where the tissue is a portion of an endocardial wall of the heart of the patient, the hook mechanism can have a curved shape configured to engage the complex anatomy of the endocardial wall to pull the electrode into contact with the endocardial wall to facilitate cardiac pacing.

Additional aspects of the present disclosure are directed generally to methods and systems for implanting stimulation assemblies. In several of the embodiments described below, for example, a method of implanting a stimulation assembly at a target site of tissue within a patient includes threading a suture into and back out of the tissue proximate the target site. The method can further include advancing the stimulation assembly along the suture until an electrode of the stimulation assembly contacts the tissue at the target site. Lastly, the method can include securing the suture to itself at a securement region proximal of the receiver-stimulator, and severing the suture proximal of the securement region. In some embodiments, the method can include advancing the stimulation assembly at least partially through a catheter while advancing the stimulation electrode along the suture. After advancing the stimulation assembly along the suture until the electrode of the stimulation assembly contacts the tissue at the target site, the method can then include directing acoustic energy toward the stimulation assembly from an acoustic transducer positioned at a distal portion of the catheter. The stimulation assembly can receive the acoustic energy and convert the acoustic energy to electrical energy for output to the tissue via the electrode. In some aspects of the present technology, the output electrical energy can stimulate the tissue and/or can be used to determine one or more one or more electrical timing parameters and/or pacing threshold parameters of the target site.

Specific details of several embodiments of the present technology are described herein with reference to FIGS. 1-4I. The present technology, however, can be practiced without some of these specific details. In some instances, well-known structures and techniques often associated with leadless tissue stimulation systems, cardiac pacing, electronic circuitry, acoustic and radiofrequency transmission and receipt, delivery systems and catheters, and the like, have not been shown in detail so as not to obscure the present technology. Moreover, although many of the embodiments are described below with respect to systems and methods for left ventricular (LV) cardiac pacing, other applications and other embodiments in addition to those described herein are within the scope of the technology. For example, one of ordinary skill in the art will understand that one or more aspects of the present technology are applicable to other implantable devices configured to treat other areas of the human body.

The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements can be arbitrarily enlarged to improve legibility. Component details can be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

FIG. 1 is a schematic diagram of a tissue stimulation system 100 ("system 100") in accordance with embodiments of the present technology. In the illustrated embodiment, the system 100 is configured to stimulate a heart 102 within a body 104 of a human patient. The system 100 can include one or more receiver-stimulators 110 (one shown in FIG. 1; which can also be referred to as stimulators, stimulation assemblies, ultrasound receivers, stimulating electrodes, stimulation electrodes, pacing electrodes, acoustic receivers, and the like) in operable communication (e.g., wireless and/or radio communication) with a controller-transmitter 120 (which can also be referred to as an ultrasound transmitter, a pulse generator, an acoustic transmitter, and the like). The controller-transmitter 120 can include a battery module 122 and a transmitter module 124 operably coupled to and powered via the battery module 122. In some embodiments, both the receiver-stimulator 110 and the controller-transmitter 120 are configured to be implanted within the body 104 of the human patient. For example, the receiver-stimulator 110 can be implanted at and/or proximate the heart 102 (e.g., in the left ventricle, the right ventricle, or proximate area) for delivering stimulation pulses to the heart 102, while the controller-transmitter 120 can be positioned at another location remote from the heart 102 (e.g., in the chest area). In a particular embodiment, the receiver-stimulator 110 can be implanted within endocardial tissue of the left ventricle. The transmitter module 124 of the controller-transmitter 120 is configured to direct energy (e.g., acoustic energy, ultrasound energy) toward the receiver-stimulator 110, which is configured to receive the energy and deliver one or more electrical pulses (e.g., stimulation pulses, pacing pulses) to the heart 102.

In some embodiments, the system 100 can further include a programmer 130 in operable communication with the controller-transmitter 120. The programmer 130 can be positioned outside the body 104 and can be operable to program various parameters of the controller-transmitter 120 and/or to receive diagnostic information from the controller-transmitter 120. In some embodiments, the system 100 can further include a co-implant device 132 (e.g., an implantable cardioverter defibrillator (ICD) or pacemaker) coupled to pacing leads 134 for delivering stimulation pulses to one or more portions of the heart 102 other than the area stimulated by the receiver-stimulator 110. In other embodiments, the co-implant device 132 can be a leadless pacemaker which is implanted directly into the heart 102 to eliminate the need for separate pacing leads 134. The co-implant device 132 and the controller-transmitter 120 can be configured to operate in tandem and deliver stimulation signals to the heart 102 to cause a synchronized heartbeat. In some embodiments, the controller-transmitter 120 can receive signals (e.g., electrocardiogram signals) from the heart 102 to determine information related to the heart 102, such as a heart rate, heart rhythm, including the output of the pacing leads 134 located in the heart 102. In some embodiments, the controller-transmitter 120 can alternatively or additionally be configured to receive information (e.g., diagnostic signals) from the receiver-stimulator 110. The received signals can be used to adjust the ultrasound energy signals delivered to the receiver-stimulator 110.

The receiver-stimulator 110, the controller-transmitter 120, and/or the programmer 130 can include a machine-readable (e.g., computer-readable) or controller-readable medium containing instructions for generating, transmitting, and/or receiving suitable signals (e.g., stimulation signals, diagnostic signals). The receiver-stimulator 110, the controller-transmitter 120, and/or the programmer 130 can include one or more processor(s), memory unit(s), and/or input/output device(s). Accordingly, the process of providing stimulation signals and/or executing other associated functions can be performed by computer-executable instructions contained by, on, or in computer-readable media located at the receiver-stimulator 110, the controller-transmitter 120, and/or the programmer 130. Further, the receiver-stimulator 110, the controller-transmitter 120, and/or the programmer 130 can include dedicated hardware, firmware, and/or software for executing computer-executable instructions that, when executed, perform any one or more methods, processes, and/or sub-processes described herein. The dedicated hardware, firmware, and/or software also serve as "means for" performing the methods, processes, and/or sub-processes described herein.

In some embodiments, the system 100 can include several features generally similar or identical to those of the leadless tissue stimulation systems disclosed in (i) U.S. Pat. No. 7,610,092, filed Dec. 21, 2005, and titled "LEADLESS TISSUE STIMULATION SYSTEMS AND METHODS," (ii) U.S. Pat. No. 8,315,701, filed Sep. 4, 2009, and titled "LEADLESS TISSUE STIMULATION SYSTEMS AND METHODS," and/or (iii) U.S. Pat. No. 8,718,773, filed May 23, 2007, and titled "OPTIMIZING ENERGY TRANSMISSION IN A LEADLESS TISSUE STIMULATION SYSTEM."

Figure 2A:
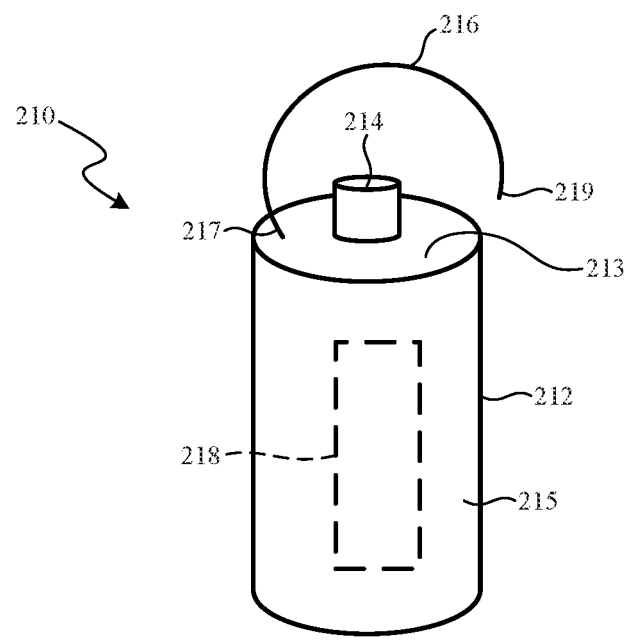
FIG. 2A is a partially schematic side view of a receiver-stimulator in accordance with embodiments of the present technology.

FIG. 2A is a partially schematic side view of a receiver-stimulator 210 in accordance with embodiments of the present technology. In some embodiments, the receiver-stimulator 210 can operate in the environment of FIG. 1. For example, the receiver-stimulator 210 can be implanted at the heart 102 and can be configured to receive acoustic energy (e.g., ultrasound energy) from the controller-transmitter 120 and to deliver one or more electrical pulses to the heart 102 based on the received acoustic energy.

More specifically, in the illustrated embodiment the receiver-stimulator 210 includes a body 212 having a distal surface 213 (e.g., a distal portion) and a side surface 215. In some embodiments, the body 212 can have a generally cylindrical shape while, in other embodiments, the body 212 can have other shapes (e.g., including a rectangular, square, polygonal, rectilinear, irregular, and/or other cross-sectional shape). The receiver-stimulator 210 can further include an electrode 214 positioned at (e.g., coupled to, extending from) the distal surface 213 of the body 212 and a hook mechanism 216 (e.g., an anchor mechanism, a tether mechanism) positioned at the distal surface 213. In some embodiments the electrode 214 is a cathode and all or a portion of the body 212 of the receiver-stimulator 210 can comprise an anode. As described in detail above with reference to FIG. 1, the receiver-stimulator 210 can include circuitry 218 configured to (i) receive energy (e.g., directed acoustic energy) from the controller-transmitter 110 (FIG. 1), (ii) convert the energy to electrical energy, and (iii) output the electrical energy via the electrode 214 to simulate tissue of a patient adjacent the electrode 214.

In some embodiments, the receiver-stimulator 210 can include some features that are at least generally similar in structure and function, or identical in structure and function, to those of the receiver-stimulators disclosed in any of (i) U.S. Pat. No. 7,848,815, filed Sep. 4, 2009, and titled "IMPLANTABLE TRANSDUCER DEVICES"; (ii) U.S. Pat. No. 7,606,621, filed Dec. 21, 2005, and titled "IMPLANTABLE TRANSDUCER DEVICES"; (iii) U.S. Pat. No. 7,610,092, filed Dec. 21, 2005, and titled "LEADLESS TISSUE STIMULATION SYSTEMS AND METHODS"; (iv) U.S. Pat. No. 9,616,237, filed Sep. 30, 2013, and titled "SYSTEMS, DEVICES, AND METHODS FOR SELECTIVELY LOCATING IMPLANTABLE DEVICES"; (v) U.S. Pat. No. 9,343,654, filed Oct. 15, 2015, and titled "METHOD OF MANUFACTURING IMPLANTABLE WIRELESS ACOUSTIC STIMULATORS WITH HIGH ENERGY CONVERSION EFFICIENCIES"; and/or (vi) U.S. Pat. No. 9,283,392, filed Sep. 24, 2010, and titled "TEMPORARY ELECTRODE CONNECTION FOR WIRELESS PACING SYSTEMS," each of which is incorporated herein by reference in its entirety.

In the illustrated embodiment, the hook mechanism 216 includes a first portion 217 secured to and/or proximate to the distal surface 213 of the body 212 and a second portion 219 that is free. The hook mechanism 216 can have a curved shape between the first and second portions 217, 219 such that, for example, the second portion 219 points at least partially back toward the body 212. The curve of the hook mechanism 216 can be circular, oval, polygonal, and/or other shapes. In the illustrated embodiment, the hook mechanism 216 lays in a plane that extends generally orthogonal to the distal surface 213. In some embodiments, the second portion 219 of the hook mechanism 216 can have a sharpened distal tip or terminus to enable the hook mechanism 216 to penetrate tissue. The hook mechanism 216 can be formed of a metal, plastic, and/or suitably strong materials. In some embodiments, the hook mechanism 216 is rigid such that the hook mechanism 216 is not configured to move substantially relative to the body 212. In other embodiments, the hook mechanism 216 can be formed of a flexible material such that, for example, the hook mechanism 216 is biased in a direction toward the body 212 and the electrode 214.

In some embodiments, the first portion 217 of the hook mechanism 216 is not permanently secured to the body 212 such that the hook mechanism 216 is movable relative to the body 212. For example, the hook mechanism 216 can be movable from a delivery position (not shown) in which all or a portion of the hook mechanism 216 is positioned within the body 212 or against an outer surface of the body 212, to a deployed position shown in FIG. 2 in which the hook mechanism 216 extends away from the body 212. In some embodiments, the receiver-stimulator 210 can be advanced to a target site within a patient (e.g., a target site within the left ventricle of a human patient) in the delivery position before being moved to the deployed position.

Figure 2B:
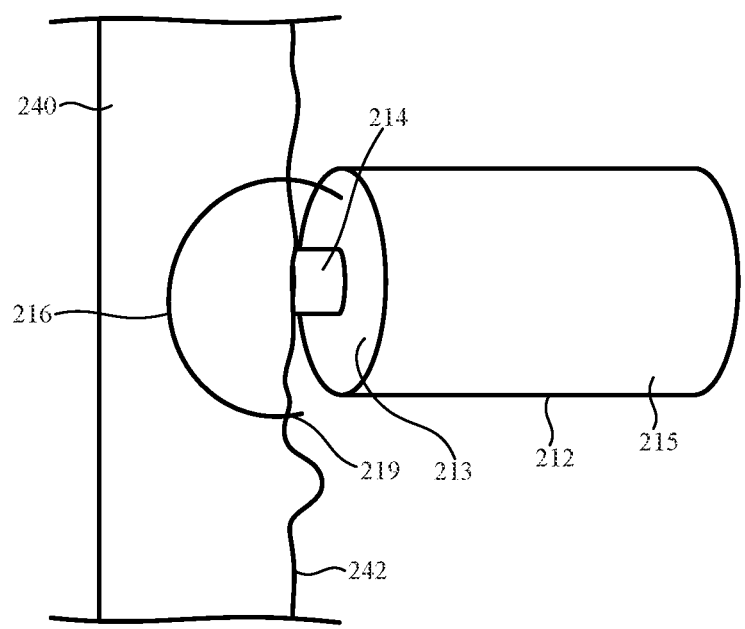
FIG. 2B is a side view of the receiver-stimulator of FIG. 2A secured to tissue of a patient in accordance with embodiments of the present technology.

When the receiver-stimulator 210 is implanted within a patient, the hook mechanism 216 is configured to secure the receiver-stimulator 210 in position relative to tissue of the patient such that the electrode 214 contacts the tissue. FIG. 2B, for example, is a side view of the receiver-stimulator 210 implanted at tissue 240 of a patient in accordance with embodiments of the present technology. In some embodiments, the tissue 240 can be cardiac tissue, such as tissue of the left ventricle of a human patient, and can define an endocardial wall 242. In the illustrated embodiment, the hook mechanism 216 extends into the tissue 240 to pull the electrode 214 and the tissue 240 toward one another. That is, for example, the hook mechanism 216 can pull the electrode 214 into contact (e.g., electrical engagement) with the endocardial wall 242. In some embodiments, the second portion 219 of the hook mechanism 216 can extend out of the tissue 240 while, in other embodiments, the second portion 219 can be positioned within the tissue 240 after implantation.

In some embodiments, such as when the tissue 240 comprises cardiac tissue, the endocardial wall 242 can have a complex structure comprised of trabeculae, papillary muscles, chordae, etc., that define a fractal-like surface including various openings, depressions, caves, and the like. In some aspects of the present technology, after implantation the hook mechanism 216 is configured to pull the electrode 214 into proper contact with the endocardial wall 242, such as contact with the papillary muscles, to facilitate effective electrical stimulation thereof. For example, the hook mechanism 216 can position the electrode 214 for desired endocardial stimulation as opposed to mid-myocardial or other stimulation. Accordingly, in some aspects of the present technology the receiver-stimulator 210 is optimized for implantation at fascial pacing targets, such as the left bundle branch (LBB). In contrast, some known electrical stimulation electrodes include barbs or other poking mechanism that must be pushed into tissue to secure the electrode thereto. For example, such electrodes are often attached to a delivery system that must be deployed normal to (e.g., pushed inward at a 90° angle toward) the endocardial wall with sufficient force to secure the barb of the simulation electrode within the endocardial wall. In contrast to the present technology, such systems can require complex delivery systems to achieve the required normal positioning, and such anchoring techniques can reduce the likelihood of properly positioning the stimulation electrode relative to the endocardial wall. For example, if the wall is thin, pushing the barb inward into the wall can stretch and distend the wall and increase the likelihood that the barb penetrates the wall entirely. Likewise, pushing the barb inward may cause a stimulating tip of the stimulation electrode to be positioned too deep inside the wall where stimulation may not be purely endocardial—which is expected to be less effective than purely endocardial stimulation.

Figure 3A:
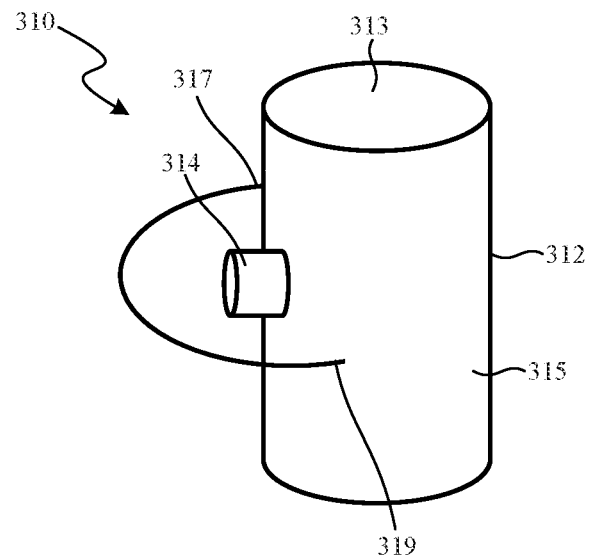
FIGS. 3A and 3B are a side view and a top view, respectively, of a receiver-stimulator in accordance with additional embodiments of the present technology.
Figure 3B:
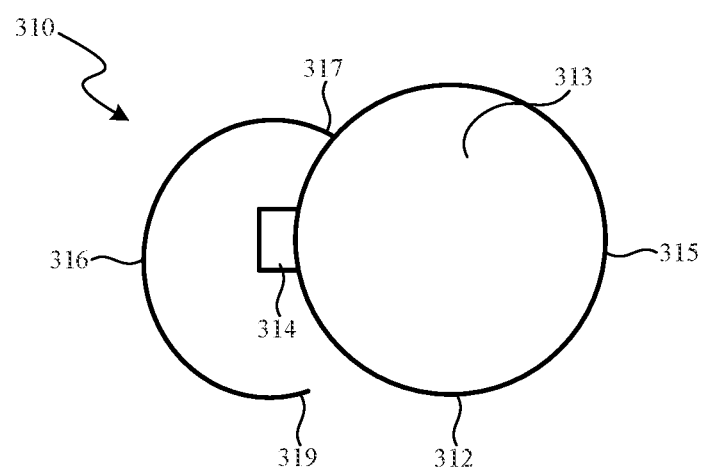

FIGS. 3A and 3B are a side view and a top view, respectively, of a receiver-stimulator 310 in accordance with additional embodiments of the present technology. The receiver-stimulator 310 (i) can operate in the environment of FIG. 1, (ii) can include some features that are at least generally similar in structure and function, or identical in structure and function, to the corresponding features of the receiver-stimulator 210 described in detail above with reference to FIGS. 2A and 2B, and/or (iii) can operate in a generally similar or identical manner to the receiver-stimulator 210. For example, referring to FIGS. 3A and 3B together, the receiver-stimulator 310 includes a body 312 having a distal surface 313 and a side surface 315, an electrode 314, and a hook mechanism 316.

However, in the illustrated embodiment the electrode 314 and the hook mechanism 316 extend from the side surface 315. The hook mechanism 316 can include a first portion 317 secured to the side surface 315 of the body 312 and a second portion 319 that is free. When the receiver-stimulator 310 is implanted within a patient, the hook mechanism 316 is configured to secure the receiver-stimulator 310 in position relative to tissue of the patient such that the electrode 314 contacts the tissue. For example, the hook mechanism 316 can pull the electrode 314 into contact (e.g., electrical engagement) with the tissue (e.g., the endocardial wall 242 of FIG. 2B). In the illustrated embodiment, the hook mechanism 316 extends generally parallel to (e.g., concentric to, is positioned in a plane generally parallel to) the side surface 315 and the distal surface 313. In other embodiments, the hook mechanism 316 can extend at an angle relative to the side surface 315 to, for example, control an orientation of the body 312 relative to the tissue at a target implantation site. In some such embodiments, the receiver-stimulator 310 can be non-isotropically directed.

Referring to FIGS. 2A-3B together, in some embodiments a receiver-stimulator in accordance with the present technology can include multiple hook mechanisms extending from the same or different portions of the receiver-stimulator body. For example, the receiver-stimulator 210 can include multiple hook mechanisms 216 extending from the distal surface 213 of the body 212 and/or can include one or more hook mechanisms extending from the side surface 215 and/or another portion of the body 212. Similarly, the receiver-stimulator 310 can include multiple hook mechanisms 316 extending from the side surface 315 of the body 312 and/or can include one or more hook mechanisms extending from the distal surface 313 and/or another portion of the body 312.

FIGS. 4A-4I are side views of a distal portion of a delivery system 450 during different stages of a procedure to implant a receiver-stimulator 410 (FIGS. 4E-4I) within tissue 440 of a patient in accordance with embodiments of the present technology. In some embodiments, the tissue 440 can be cardiac tissue, such as tissue of the left ventricle of a human patient, and can define an endocardial wall 442.

FIG. 4A illustrates the delivery system 450 after advancement of a first catheter 452 (which can also be referred to as a shaft, sheath, elongate member, and the like) toward the wall 442. In some embodiments, the first catheter 452 can be advanced through the vasculature of the patient, into a heart chamber of the patient (e.g., the left ventricle), and toward the wall 442. In the illustrated embodiment, the first catheter 452 includes a distal portion 453 defining a distal terminus or tip 454. An electrode 456 can extend from the distal tip 454 and can be electrically coupled to an external monitor and pacing controller via a wireless connection and/or one or more conductive lines (not shown) routed through the first catheter 452 to allow for externally controlled monitoring and pacing. In the illustrated embodiment, the first catheter 452 further includes multiple working channels 458 (identified individually as a first working channel 458a and a second working channel 458b) that can extend fully or at least partially from the distal tip 454 through the first catheter 452.

Figure 4B:
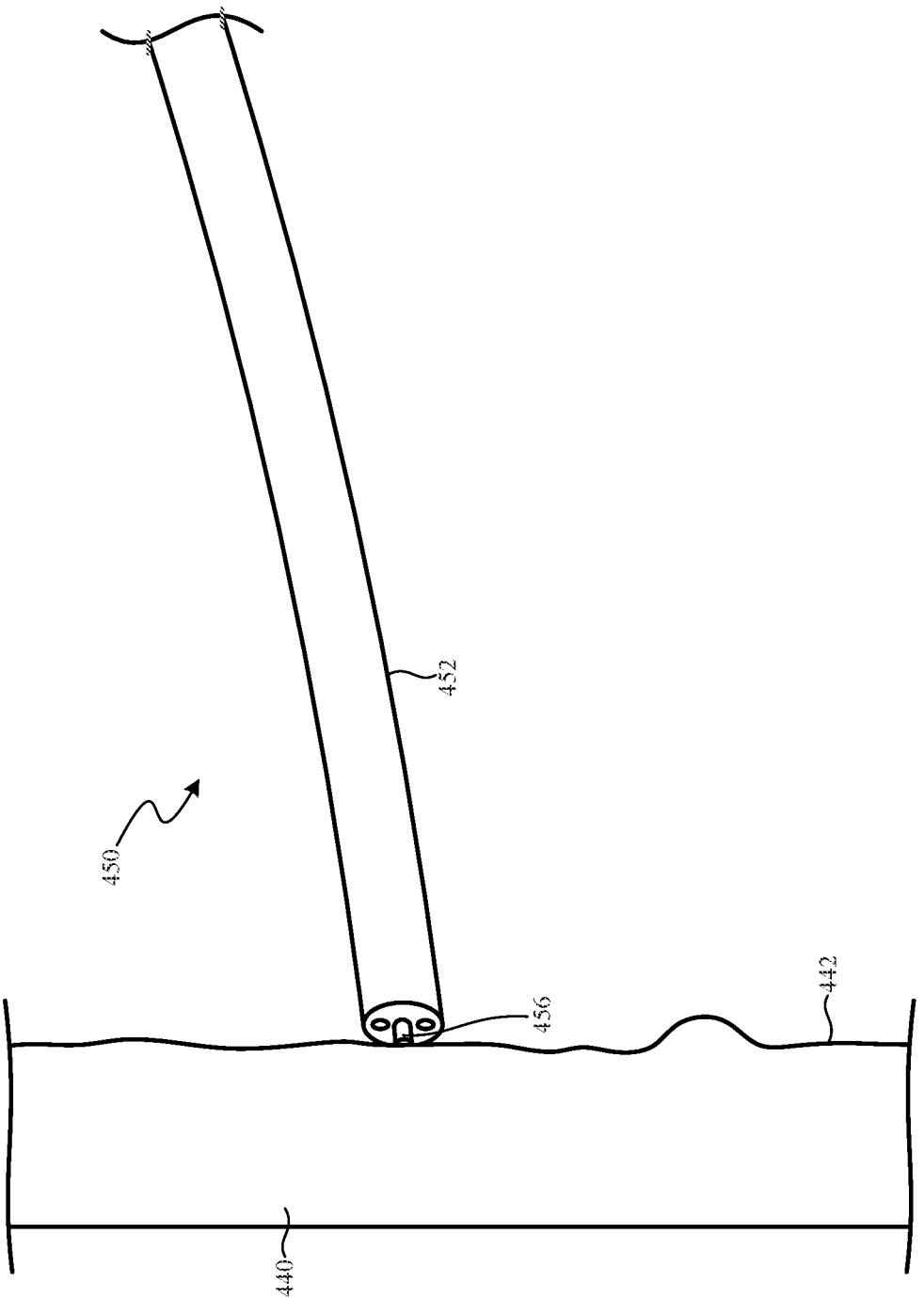

FIG. 4B illustrates the delivery system 450 after the first catheter 452 has been advanced such that the electrode 456 is in contact with the wall 442. The electrode 456 can be controlled via the external monitoring and pacing controller to electrically stimulate the tissue 440 and/or to receive electrical signals from the tissue 440. In some embodiments, the electrode 456 can be used to map and/or electrically pace the tissue 440 to determine a target site for the subsequent implantation of a stimulation electrode (e.g., the receiver-stimulator 410 of FIGS. 4E-4I). For example, the delivery system 450 can be used to measure and analyze electrical timing parameters and/or pacing threshold parameters at the target site. In some embodiments, such a determination can be made using any of the methods disclosed in U.S. Pat. No. 9,283,392, filed Sep. 24, 2010, and titled "TEMPORARY ELECTRODE CONNECTION FOR WIRELESS PACING SYSTEMS," which is incorporated herein by reference in its entirety. In some embodiments, the first catheter 452 can be moved relative to the wall 442 to position the electrode 456 in contact with one or more different portions of the wall 442 to test different target sites for implantation of the stimulation electrode. In some embodiments, the electrode 456 can emulate the position and size of an electrode of the subsequently implanted receiver-stimulator 410 (FIGS. 4E-4I).

Figure 4C:
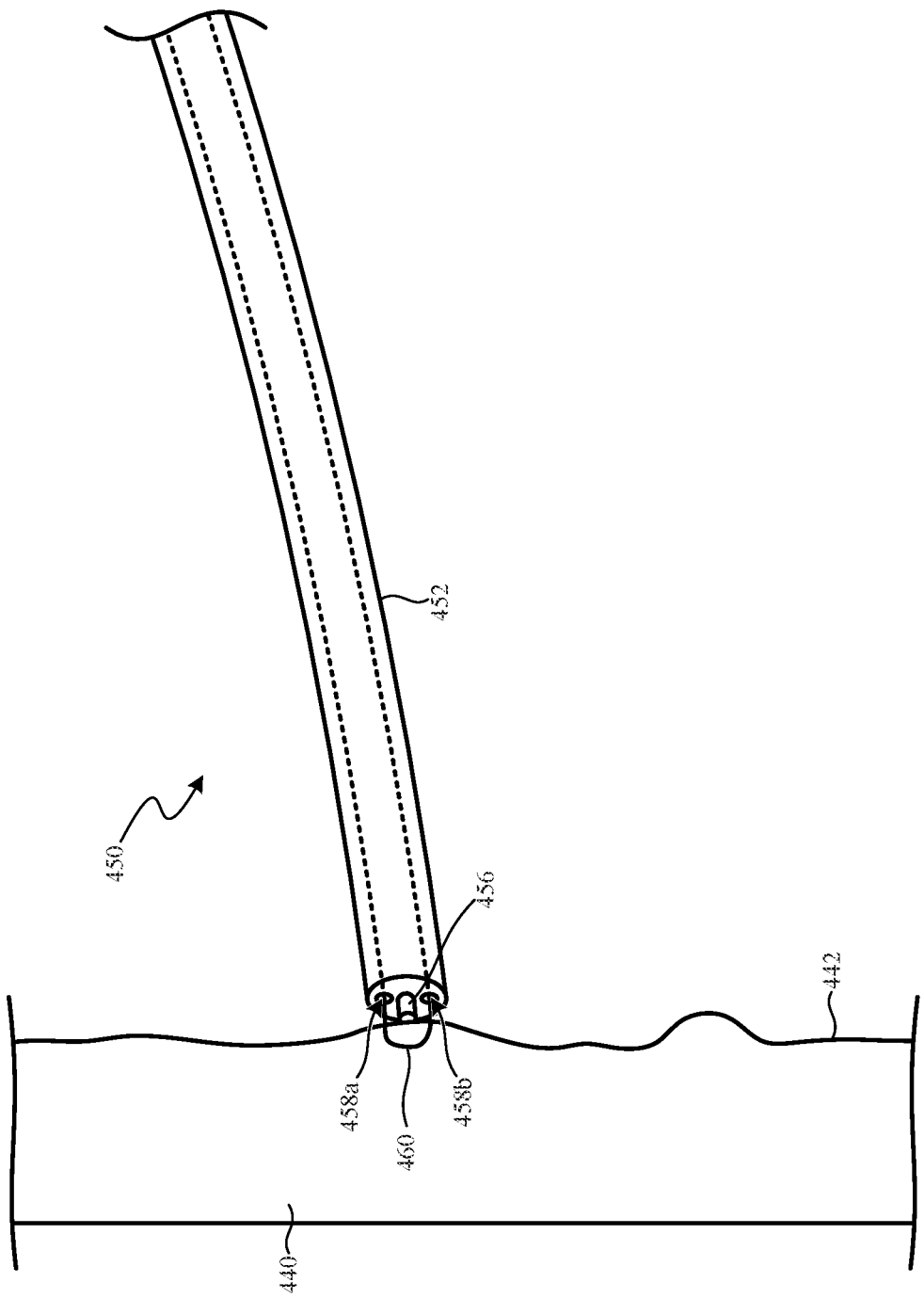

FIG. 4C illustrates the delivery system 450 after selection of a target site along the wall 442, and after advancement of a suture 460 through the working channels 458 of the first catheter 452 and into the tissue 440 (e.g., into the myocardium). In some embodiments, the suture 460 can be advanced through the first working channel 458a, into the wall 442 and through the tissue 440, and back out of the tissue 440 into the second working channel 458b. The suture 460 can extend entirely through the first catheter 452 such that first and second end portions of the suture 460 (not shown) are positioned proximally outside the patient. In some embodiments, the suture 460 (e.g., one end portion thereof) can be coupled to a rigid member (not shown), such as a needle or other member, that can be advanced through the first working channel 458a, the tissue 440, and the second working channel 458b to thread the suture 460 along the path illustrated in FIG. 4C.

In some embodiments, after securing the suture 460 to the tissue 440, the suture 460 can be tightened to bring the electrode 456 into firm contact with the wall 442 at the target site. The electrode 456 can then be controlled again to confirm electrical timing parameters and/or pacing threshold parameters at the target site. In some aspects of the present technology, the location of the electrode 456 after deployment of the suture 460 can be substantially the same as the final implantation location of the receiver-stimulator 410 (FIGS. 4E-4I).

Figure 4D:
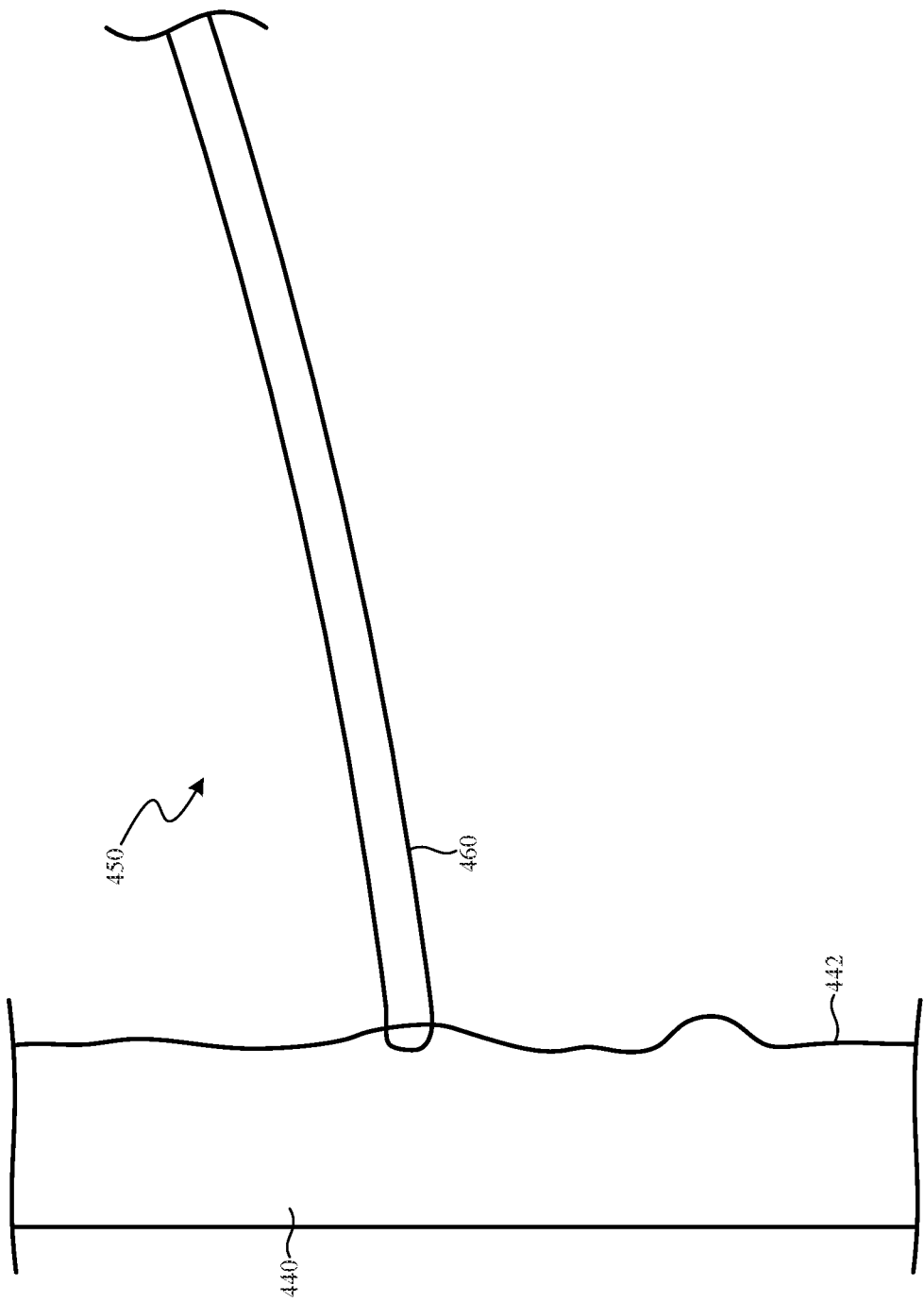

FIG. 4D illustrates the delivery system 450 after removal (e.g., withdrawal) of the first catheter 452 (FIG. 4C). After removal of the first catheter 452, the suture 460 can remain in position within the tissue 440 of the patient and can extend proximally to outside the patient.

Figure 4E:
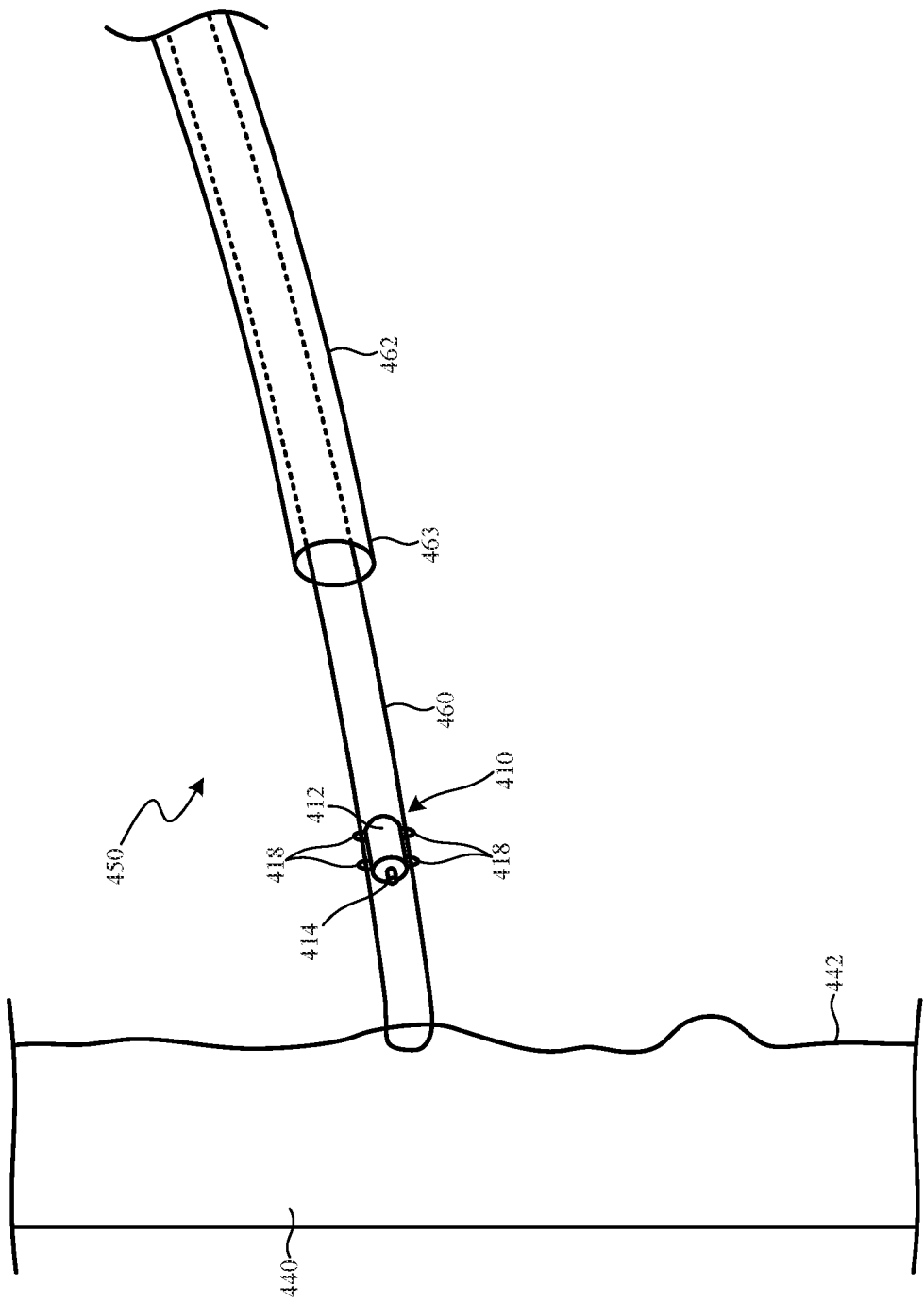

FIG. 4E illustrates the delivery system 450 after (i) advancement of a second catheter 462 over the suture 460 and toward the wall 442 and (ii) advancement of a receiver-stimulator 410 over the suture 460 from a distal portion 463 of the second catheter 462 and toward the wall 442. In some embodiments, the receiver-stimulator 410 can include some features that are at least generally similar in structure and function, or identical in structure and function, to those of the receiver-stimulators 110, 210, and/or 310 described in detail above with references to FIGS. 1-3B. For example, the receiver-stimulator 410 can include a body 412 and an electrode 414 projecting from the body 412 (e.g., a distal surface or portion thereof). In the illustrated embodiment, the receiver-stimulator 410 further includes a plurality of guides 418 extending from the body 412 (e.g., from a side surface thereof). The guides 418 can be loops, clips, and/or the like, and the suture 460 can be threaded through the guides 418 such that the receiver-stimulator 410 tracks over the suture 460 toward the wall 442. In some embodiments, the receiver-stimulator 410 can be advanced over the suture 460 from the distal portion 463 of the second catheter 462 via an elongate pusher (not shown) that extends through the second catheter 462. In other embodiments, the receiver-stimulator 410 can be temporarily secured to the distal portion 463 of the second catheter 462 during delivery and advanced over the suture 460 via advancement of the second catheter 462.

Figure 4F:
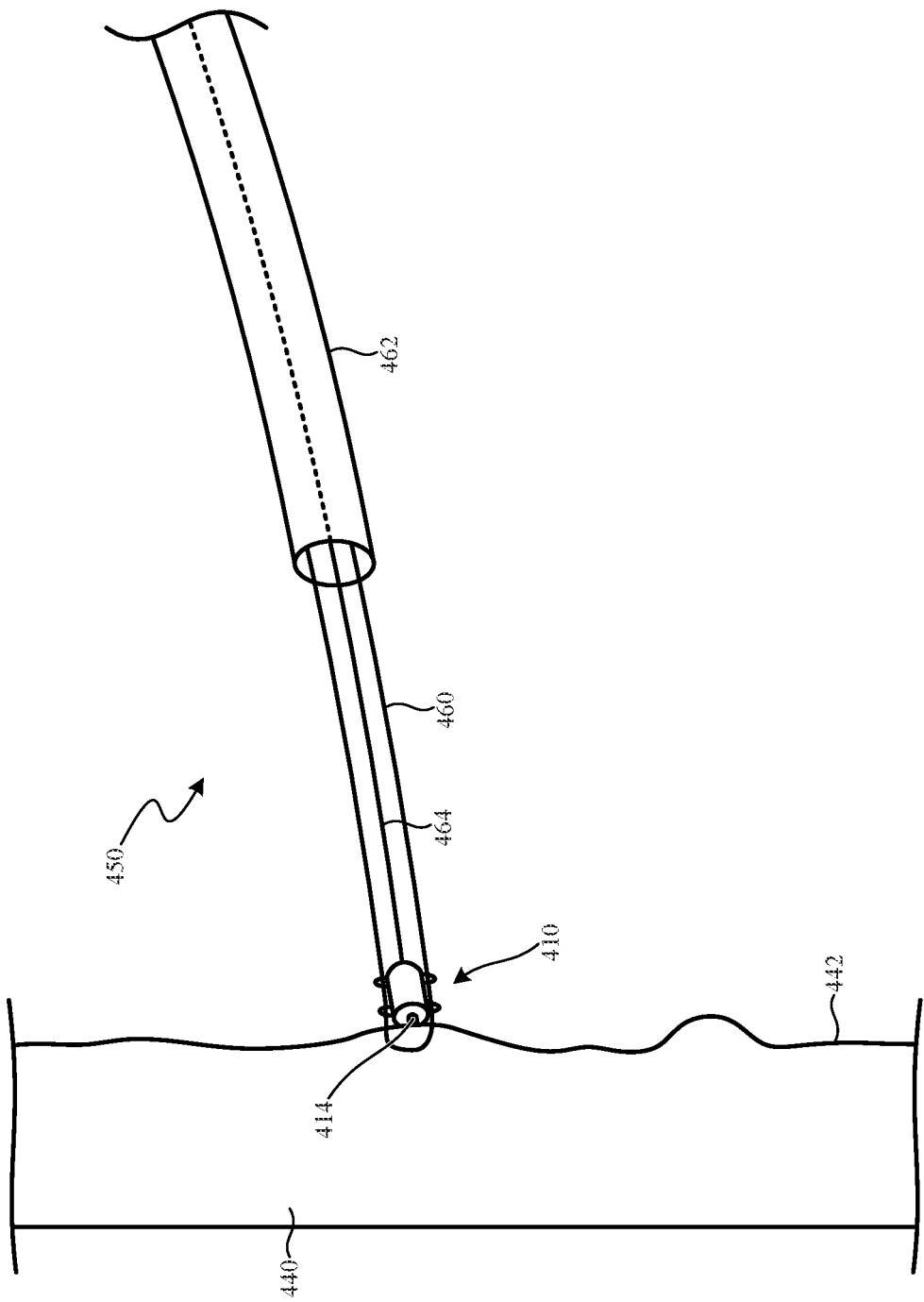
Figure 4G:
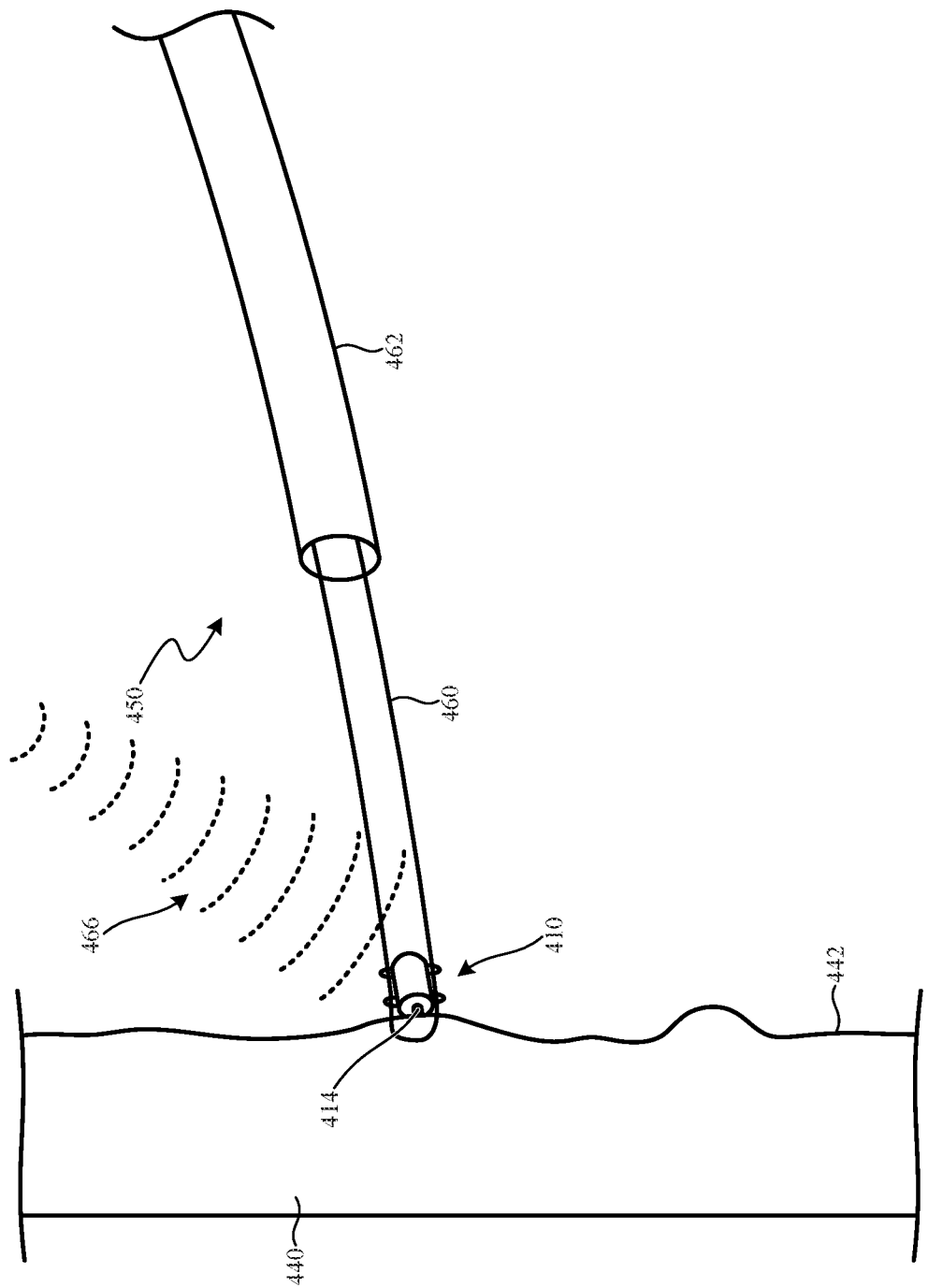
Figure 4H:
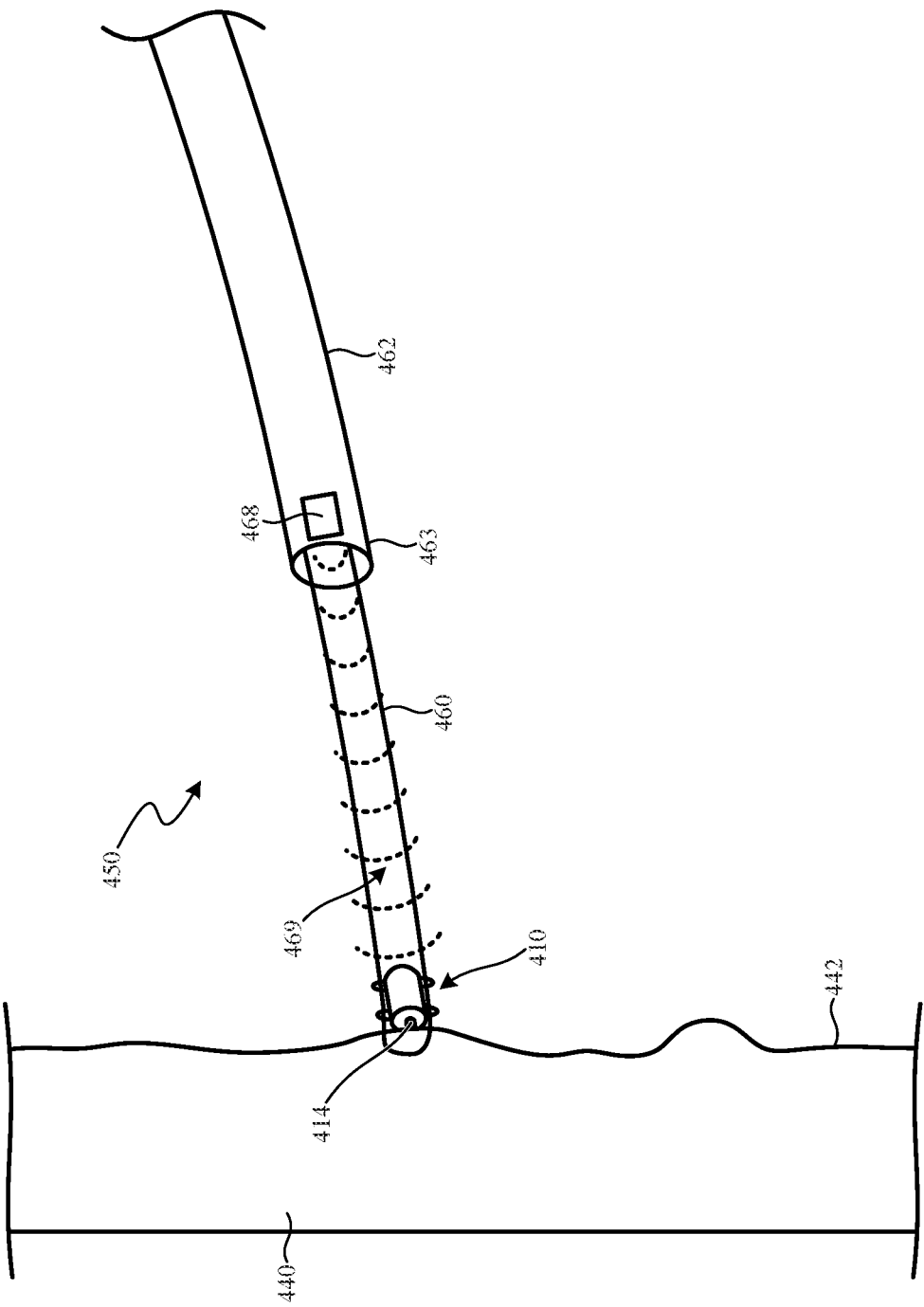

FIG. 4F-4H illustrate the delivery system 450 after further advancement of the receiver-stimulator 410 over the suture 460 toward the wall 442 until the electrode 414 contacts the wall 442. Referring to FIGS. 4F-4H together, the electrode 414 can be positioned proximal to the location of the suture 460 within the tissue 440. In some aspects of the present technology, such positioning can inhibit fibrotic growth at position of the electrode 414. In other embodiments, the electrode 414 can be positioned on or formed as a portion of the suture 460 itself.

In some embodiments, the delivery system 450 can include various features configured to facilitate a final confirmation of electrical timing parameters and/or pacing threshold parameters at the location of the receiver-stimulator 410. More specifically, referring first to FIG. 4F, in some embodiments the receiver-stimulator 410 can be temporarily connected to the external monitor and pacing controller via one or more conductive lines 464 that extend through the second catheter 462. The external monitor and pacing controller can be used to control the electrode 414 to stimulate the tissue 440 and/or to detect the electrical timing parameters and/or the pacing threshold parameters. Referring next to FIG. 4G, in some embodiments the receiver-stimulator 410 can receive acoustic energy 466 from the controller-transmitter 120 (FIG. 1). The receiver-stimulator 410 can convert the received acoustic energy 466 to electrical energy and can deliver the electrical energy to the tissue 440 via the electrode 414. The controller-transmitter 120 can detect the delivered electrical energy and/or various electrical parameters of the patient (e.g., the heart of the patient) to determine the electrical timing parameters and/or the pacing threshold parameters.

Referring to FIG. 4H, in some embodiments the second catheter 462 can include an acoustic transducer 468 positioned at and/or proximate the distal portion 463 of the second catheter 462. In some embodiments, the acoustic transducer 468 can be an ultrasound transducer. The acoustic transducer 468 can be configured to generate acoustic energy 469 and to direct the acoustic energy 469 from the distal portion 463 of the second catheter 462 toward the receiver-stimulator 410. The receiver-stimulator 410 can receive the acoustic energy 469, convert the received acoustic energy 469 to electrical energy, and deliver the electrical energy to the tissue 440 via the electrode 414. The controller-transmitter 120 and/or another component of the system can detect the delivered electrical energy and/or various electrical parameters of the patient (e.g., the heart of the patient) to determine the electrical timing parameters and/or the pacing threshold parameters.

In some embodiments, the receiver-stimulator 410 can include a voltage regulator configured to limit the electrical output of the electrode 414 to at or below a predetermined level (e.g., about 3 volts). In some embodiments, the receiver-stimulator 410 and the voltage limiter can be least generally similar in structure and function, or identical in structure and function, to the receiver-stimulators and/or voltage regulators disclosed in U.S. patent application Ser. No. 16/773,599, filed Jan. 27, 2020, and titled "DEVICES, SYSTEMS, AND METHODS FOR CARDIAC RESYNCHRONIZATION THERAPY," which is incorporated herein by reference in its entirety. In such embodiments, the acoustic transducer 468 can be configured to output the acoustic energy 469 at a level sufficient to trigger the maximum voltage output of the receiver-stimulators (e.g., 3 volts). In some aspects of the present technology, this can allow the controller-transmitter 120 (FIG. 1) and/or another component of the system to measure a pulse-width threshold of the electrical output of the receiver-stimulator 410 at a fixed voltage. In some aspects of the present technology, utilizing the acoustic transducer 468 positioned at the distal portion 463 of the second catheter 462 can reduce the complexity of the delivery system 450 as compared to, for example, the temporary electrical connection embodiment illustrated in FIG. 4F. In some embodiments, the delivery system 450 can utilize multiple ones of (e.g., a combination of) the above-described features illustrated in FIGS. 4F-4H to determine and confirm the electrical timing parameters and/or the pacing threshold parameters at the target site.

Figure 4I:
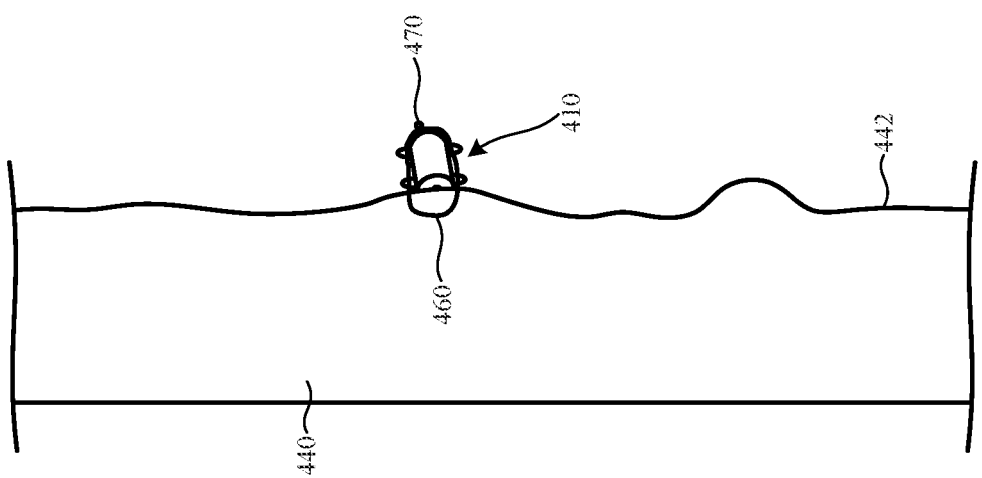

FIG. 4I illustrates the delivery system 450 after (i) securing the suture 460 to itself at a securement region 470 proximal of the receiver-stimulator 410 to secure the receiver-stimulator 410 in position against the wall 442 at the target site, (ii) cutting of the suture 460 proximal to the securement region 470, and (iii) removal of the second catheter 462 from the patient. At this stage, the suture 460 can tightly secure the receiver-stimulator 410 against the tissue 440. In some embodiments, securing the suture 460 to itself can include tying or crimping the suture 460 such that the securement region 470 comprises a knot or crimp. In some embodiments, one or more tools and/or manipulators (not shown) can be advanced through the second catheter 462 to facilitate securing, tying, crimping, and/or cutting of the suture 460.

The following examples are illustrative of several embodiments of the present technology:

1. A stimulation assembly implantable within a heart of a patient, comprising:
   a body;
   circuitry positioned at least partially within the body and configured to receive acoustic energy from an external source and convert the acoustic energy to electrical energy;

an electrode carried by the body and configured to deliver the electrical energy to cardiac tissue of the patient; and a hook mechanism coupled to the body, wherein the hook mechanism is configured to engage the cardiac tissue to pull the cardiac tissue and the electrode toward and into engagement with one another.

2. The stimulation assembly of example 1 wherein the body has a cylindrical shape including a distal surface and a side surface, and wherein the hook mechanism extends from the distal surface.

3. The stimulation assembly of example 2 wherein the electrode extends from the distal surface.

4. The stimulation assembly of example 1 wherein the body has a cylindrical shape including a distal surface and a side surface, and wherein the hook mechanism extends from the side surface.

5. The stimulation assembly of example 4 wherein the electrode extends from the side surface.

6. The stimulation assembly of example 4 or example 5 wherein the hook mechanism extends within a plane extending generally parallel to the distal surface.

7. The stimulation assembly of any one of examples 1-6 wherein the hook mechanism has a first end portion coupled to the body and a second end portion that is free, and wherein the hook mechanism has a curved shape between the first and second end portions.

8. The stimulation assembly of example 7 wherein the second portion of the hook mechanism points at least partially back toward the body.

9. The stimulation assembly of any one of examples 1-8 wherein hook mechanism is movable between a delivery position and a deployed position, wherein the hook mechanism is positioned at least partially within the body in the delivery position, and wherein the hook mechanism extends from the body in the deployed position.

10. A method of implanting a stimulation assembly at a target site of cardiac tissue within a patient, the method comprising:

threading a suture into and back out of the cardiac tissue proximate the target site;

advancing the stimulation assembly along the suture until an electrode of the stimulation assembly contacts the cardiac tissue at the target site;

securing the suture to itself at a securement region proximal of the stimulation assembly; and severing the suture proximal of the securement region.

11. The method of example 10 wherein the method further comprises detecting one or more electrical timing parameters and/or pacing threshold parameters at the target site.

12. The method of example 11 wherein detecting the one or more electrical timing parameters and/or pacing threshold parameters includes positioning an electrode of a catheter in contact with the target site before threading the suture into and back out of the tissue.

13. The method of example 12 wherein threading the suture into and back out of the tissue includes advancing the suture out of the catheter, into the tissue, back out of the tissue, and then back into the catheter.

14. The method of any one of examples 10-13 wherein the stimulation assembly includes a body and a plurality of guides coupled to the body, wherein the method further comprises threading the suture trough the guides, and wherein advancing the stimulation assembly along the suture includes tracking the guides along the suture.

15. The method of any one of examples 10-14 wherein securing the suture to itself includes tying or crimping the suture.

16. The method of any one of examples 10-15 wherein the method further comprises:

advancing the stimulation assembly at least partially through a catheter and along the suture;

after advancing the stimulation assembly along the suture until the electrode of the stimulation assembly contacts the tissue at the target site, directing acoustic energy toward the stimulation assembly from an acoustic transducer positioned at a distal portion of the catheter;

converting, at the stimulation assembly, the acoustic energy to electrical energy; and outputting the electrical energy to the tissue via the electrode.

17. A system for stimulating cardiac tissue of a patient, comprising:

a delivery catheter having a distal portion, wherein the delivery catheter is configured to at least partially advance an implantable stimulation assembly through the vasculature of the patient to the cardiac tissue; and an acoustic transducer coupled to the distal portion of the delivery catheter, wherein the acoustic transducer is configured to generate acoustic energy and to direct the acoustic energy toward the stimulation assembly when an electrode of the stimulation assembly contacts the tissue of the patient.

18. The system of example 17, further comprising the stimulation assembly, wherein the stimulation assembly includes circuitry configured to receive the acoustic energy, convert the acoustic energy to electrical energy, and output the electrical energy to the electrode for delivery to the cardiac tissue.

19. The system of example 18 wherein the circuitry of the stimulation assembly further includes a voltage limiter configured to limit a voltage of the electrical energy output to the electrode to at or below a predetermined level.

20. The system of example 19 wherein the acoustic transducer is configured to generate the acoustic energy at a level sufficient to cause the circuitry of the stimulation assembly to output the electrical energy at the predetermined level.

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments can perform steps in a different order. Likewise, the various electronic components and functions can be separated into more or fewer electronic circuit elements and/or functional blocks. The various components and/or functionalities of the embodiments described herein can also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms can also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications can be made without deviating from the technology. Further, while advantages associated with some embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

I claim:

1. A method of implanting a stimulation assembly at a target site of cardiac tissue within a patient, the method comprising:
    threading a suture into and back out of the cardiac tissue proximate the target site by advancing the suture out of a catheter, into the cardiac tissue, back out of the cardiac tissue, and then back into the catheter;
    advancing the stimulation assembly along the suture until an electrode of the stimulation assembly contacts the cardiac tissue at the target site;
    securing the suture to itself at a securement region proximal of the stimulation assembly; and
    severing the suture proximal of the securement region.

2. The method of claim 1 wherein the method further comprises detecting one or more electrical timing parameters and/or pacing threshold parameters at the target site.

3. The method of claim 2 wherein detecting the one or more electrical timing parameters and/or pacing threshold parameters includes positioning an electrode of a catheter in contact with the target site before threading the suture into and back out of the cardiac tissue.

4. The method of claim 1 wherein the stimulation assembly includes a body and a plurality of guides coupled to the body, wherein the method further comprises threading the suture through the guides, and wherein advancing the stimulation assembly along the suture includes tracking the guides along the suture.

5. The method of claim 1 wherein securing the suture to itself includes tying or crimping the suture.

6. The method of claim 1 wherein the method further comprises:
    advancing the stimulation assembly at least partially through a catheter and along the suture;
    after advancing the stimulation assembly along the suture until the electrode of the stimulation assembly contacts the cardiac tissue at the target site, directing acoustic energy toward the stimulation assembly from an acoustic transducer positioned at a distal portion of the catheter;
    converting, at the stimulation assembly, the acoustic energy to electrical energy; and
    outputting the electrical energy to the cardiac tissue via the electrode.

7. The method of claim 1 wherein the method further comprises:
    receiving acoustic energy at the stimulation assembly from a remote source;
    converting the acoustic energy to electrical energy at the stimulation assembly; and
    outputting the electrical energy to the cardiac tissue via the electrode.

8. The method of claim 1 wherein the target site is along an outer surface of the cardiac tissue.

9. The method of claim 4 wherein the guides are coupled to an outer surface of the body.

10. The method of claim 4 wherein the guides comprise loops coupled to an outer surface of the body.

11. The method of claim 4 wherein the guides comprise loops coupled to an outer side surface of the body.

12. A method of implanting a stimulation assembly at a target site of cardiac tissue within a patient, the method comprising:
    threading a suture into and back out of the cardiac tissue proximate the target site;
    advancing the stimulation assembly along the suture until an electrode of the stimulation assembly contacts the cardiac tissue at the target site;
    securing the suture to itself at a securement region proximal of the stimulation assembly;
    severing the suture proximal of the securement region;
    receiving acoustic energy at the stimulation assembly from a remote source;
    converting the acoustic energy to electrical energy at the stimulation assembly; and
    outputting the electrical energy to the cardiac tissue via the electrode.

13. The method of claim 12 wherein the target site is along an outer surface of the cardiac tissue.

14. The method of claim 12 wherein the stimulation assembly includes a body having an outer surface and a plurality of guides coupled to the outer surface of the body, wherein the method further comprises threading the suture through the guides, and wherein advancing the stimulation assembly along the suture includes tracking the guides along the suture.

15. The method of claim 12 wherein the stimulation assembly includes a body having an outer side surface and a plurality of guides coupled to the outer side surface of the body, wherein the method further comprises threading the suture through the guides, and wherein advancing the stimulation assembly along the suture includes tracking the guides along the suture.

16. The method of claim 12 wherein threading the suture into and back out of the cardiac tissue includes advancing the suture out of the catheter, into the cardiac tissue, back out of the cardiac tissue, and then back into the catheter.

17. A method of implanting a stimulation assembly at a target site of cardiac tissue within a patient, the method comprising:
    threading a suture into and back out of the cardiac tissue proximate the target site;
    threading the suture through a plurality of loops coupled to an outer surface of the stimulation assembly;
    tracking the stimulation assembly along the suture until an electrode of the stimulation assembly contacts the cardiac tissue at the target site;
    securing the suture to itself at a securement region proximal of the stimulation assembly; and
    severing the suture proximal of the securement region.

18. The method claim 17 wherein the guides comprise loops.

19. The method of claim 17 wherein the target site is along an outer surface of the cardiac tissue.

20. The method of claim 17 wherein threading the suture into and back out of the cardiac tissue includes advancing the suture out of the catheter, into the cardiac tissue, back out of the cardiac tissue, and then back into the catheter.

\* \* \* \* \*